(12) United States Patent
Jeong

(10) Patent No.: US 11,840,879 B2
(45) Date of Patent: Dec. 12, 2023

(54) DOOR SEALING UNIT FOR PREVENTING SPREAD OF HARMFUL GASES AND VIRUSES AND HINGED DOOR STRUCTURE HAVING THE SAME

(71) Applicant: Jisoo Jeong, Seoul (KR)

(72) Inventor: Jisoo Jeong, Seoul (KR)

( * ) Notice: Subject to any disclaimer, the term of this patent is extended or adjusted under 35 U.S.C. 154(b) by 0 days.

(21) Appl. No.: 18/140,903

(22) Filed: Apr. 28, 2023

(65) Prior Publication Data

US 2023/0366259 A1 Nov. 16, 2023

(30) Foreign Application Priority Data

May 11, 2022 (KR) .......................... 10-2022-0057972

(51) Int. Cl.
*E06B 7/23* (2006.01)
*A61L 2/26* (2006.01)
*A61L 2/18* (2006.01)

(52) U.S. Cl.
CPC .............. *E06B 7/2316* (2013.01); *A61L 2/18* (2013.01); *A61L 2/26* (2013.01); *A61L 2202/14* (2013.01); *A61L 2202/15* (2013.01)

(58) Field of Classification Search
CPC ..................................... E06B 7/2316
USPC ........................................ 49/490.1
See application file for complete search history.

(56) References Cited

U.S. PATENT DOCUMENTS

| 5,577,349 | A | * | 11/1996 | Rissone | ................... E06B 7/16 49/306 |
| 6,761,954 | B2 | * | 7/2004 | Hauser | ..................... B60J 10/18 49/490.1 |
| 6,966,601 | B2 | * | 11/2005 | Matsumoto | ......... B60R 13/0237 49/490.1 |
| 8,726,575 | B1 | * | 5/2014 | Vulpitta | ................ E06B 7/2314 49/470 |
| 2006/0012070 | A1 | * | 1/2006 | Fontecchio | ............... B32B 5/18 264/171.13 |
| 2009/0038228 | A1 | | 2/2009 | Lee | |
| 2012/0260579 | A1 | * | 10/2012 | DeMello | ............... E06B 7/2314 49/477.1 |

FOREIGN PATENT DOCUMENTS

| DE | 4338794 C1 * | 12/1994 | ............... E06B 3/62 |
| JP | 2008-94438 A | 4/2008 | |
| KR | 10-0729222 B | 6/2007 | |
| KR | 10-2007-0111018 A | 11/2007 | |
| KR | 20-2009-0010116 U | 10/2009 | |

(Continued)

OTHER PUBLICATIONS

Machine translation of DE-4338794-C1.*

(Continued)

*Primary Examiner* — Marcus Menezes
(74) *Attorney, Agent, or Firm* — Hauptman Ham, LLP

(57) ABSTRACT

A door sealing unit for preventing spread of harmful gases and viruses is installed on a lower end frame of a door installed in a hinged manner at a boundary between a living room and a room, and includes a fixing member having a predetermined amount of elasticity and being fitted and fixed onto the lower end frame of the door, and a sealing member formed on a lower end of the fixing member and made of a soft material, wherein the sealing member is formed to spread to both sides.

6 Claims, 13 Drawing Sheets

(56) References Cited

FOREIGN PATENT DOCUMENTS

| KR | 10-2012-0000041 A | 1/2012 |
| KR | 10-2012-0043536 A | 5/2012 |
| KR | 20-2021-0001799 U | 8/2021 |

OTHER PUBLICATIONS

Korean Office Action dated Nov. 30, 2022 for corresponding Korean Patent Application No. 10-2022-0057972, 8 pages.
Korean Notice of Allowance dated Feb. 16, 2023 for corresponding Korean Patent Application No. 10-2022-0057972, 4 pages.

* cited by examiner

DOOR SEALING UNIT FOR PREVENTING SPREAD OF HARMFUL GASES AND VIRUSES AND HINGED DOOR STRUCTURE HAVING THE SAME

CROSS-REFERENCE TO RELATED APPLICATION

This application claims priority from Korean Patent Application No. 10-2022-0057972 filed on May 11, 2022 in the Korean Intellectual Property Office, and all the benefits accruing therefrom under 35 U.S.C. 119, the contents of which in its entirety are herein incorporated by reference.

BACKGROUND

Field

The present disclosure relates to a door sealing unit for preventing spread of harmful gases and viruses and a hinged door structure having the same, and more specifically, to a door sealing unit for preventing spread of harmful gases and viruses and a hinged door structure having the same that may prevent spread of viruses of infectious diseases such as COVID-19 by efficiently sealing a space between a lower end frame of a hinged door and a floor.

Description of Related Art

After the recent outbreak of COVID-19, the pandemic period has arrived, and domestically and internationally, prompt screening of COVID-19 confirmed cases and quarantine of the screened confirmed cases is being implemented as the best way to prevent spread of infectious diseases.

The above quarantine measure may be divided into facility isolation via group facility and hospital admission, and self-isolation at home where the person resides.

The group facility and the hospital facility have spaces and are equipped with related equipment to prevent the spread of the infectious diseases such as a negative pressure room. In addition, the related equipment may include electronic equipment and the like required to maintain a negative pressure.

Because such electronic equipment is a special medical equipment and system, there is a problem that an individual cannot have and use the same.

Further, the self-isolation is a method of self-quarantine for a predetermined period of time in the home where the confirmed patient resides.

Typically, each household in a general house and a condominium generally has one or more rooms and a living room. The confirmed patient must be quarantined in a room thereof for a predetermined period of time.

A hinged door is installed in a room of each household as described above. The door has a structure of being connected to hinges installed on a door frame and pivoting to be opened and closed.

A lower end frame of such door defines a predetermined gap with the floor of the room. In addition, such gap is at various levels depending on an installed state of the door.

Therefore, when the confirmed patient is isolated in the room with the door as described above, a possibility that viruses of the infectious disease may spread to the outside via the gap between the door and the floor is very high.

However, conventionally, sealing is installed on the door frame or a blocking plate is installed on the door frame to block inflow of smoke resulted from fire. However, such schemes only prevent the inflow of the smoke in case of the fire, and there is a problem in that damage may occur to the sealing due to repeated friction with the floor resulted from repetitive opening and closing operations of the door.

In addition, conventionally, spread of harmful substances contained in the smoke cannot be prevented and ventilation cannot be achieved via the sealing installed on the door.

In addition, when the door is repeatedly opened and closed, a distal end of the blocking plate cannot make uniform contact with the floor of the room, so that the spread of the infectious disease viruses to the outside cannot be effectively prevented.

SUMMARY

The present disclosure was devised to solve the above problems, and purposes of the present disclosure are as follows.

A purpose of the present disclosure is to provide a door sealing unit for preventing spread of harmful gases and viruses that may be easily installed on a lower end frame of a hinged door in a sliding manner and use sealing members of a soft material so as to be in multiple contact with the floor to improve contact properties to prevent the spread of the infectious disease viruses and the harmful gases, and a hinged door structure having the same.

In addition, another purpose of the present disclosure is to provide a door sealing unit for preventing spread of harmful gases and viruses that may allow a lower end frame of a door and the floor to be uniformly in close contact with each other regardless of evenness of a floor surface of the room, and a hinged door structure having the same.

In addition, another purpose of the present disclosure is to provide a door sealing unit for preventing spread of harmful gases and viruses that may improve contact properties between sealing members and the floor by removing foreign substances present on the floor to which the sealing members are contacted and allow a space between the sealing members to be ventilated, so that, even when infectious bacteria infiltrate into the space between the sealing members from inside the room, the bacteria may be removed by being discharged to the outside space without spreading to the living room, and a hinged door structure having the same.

Purposes according to the present disclosure are not limited to the above-mentioned purpose. Other purposes and advantages according to the present disclosure that are not mentioned may be understood based on following descriptions, and may be more clearly understood based on embodiments according to the present disclosure. Further, it will be easily understood that the purposes and advantages according to the present disclosure may be realized using means shown in the claims or combinations thereof.

To achieve the above purposes, the present disclosure provides a door sealing unit for preventing spread of harmful gases and viruses.

One aspect of the present disclosure provides a door sealing unit for preventing spread of harmful gases and viruses installed on a lower end frame of a door installed in a hinged manner at a boundary between a living room and a room including a fixing member having a predetermined amount of elasticity and being fitted and fixed onto the lower end frame of the door, and a sealing member formed on a lower end of the fixing member and made of a soft material, wherein the sealing member is formed to spread to both sides.

In one implementation of the present disclosure, a groove for receiving the lower end frame of the door fitted thereinto in a sliding manner may be defined in the fixing member, and a width of the groove may be reduced along an upward direction.

In one implementation of the present disclosure, a lubricating oil coating layer may be further formed on an inner peripheral surface of the groove.

In one implementation of the present disclosure, a grid-shaped inner structure may be formed inside the fixing member and the sealing member, and a density of the inner structure may be greater in the fixing member than in the sealing member.

In one implementation of the present disclosure, a bottom surface of the sealing member may form a flat surface.

In one implementation of the present disclosure, embossed protrusions may be further formed on a top outer surface of the sealing member.

In one implementation of the present disclosure, an elastic wire mesh may be embedded in the fixing member.

In one implementation of the present disclosure, a sterilizing liquid supplier for supplying sterilizing liquid may be detachably installed on the fixing member, spray holes may be defined in an outer peripheral surface of the sealing member, supply holes connected to the spray holes may be defined in the fixing member and the sealing member, and the sterilizing liquid supplier is connected to one end of each of the supply holes via a tube, and, when a set period is reached, supplies the sterilizing liquid via the tube and the supply hole and sprays the sterilizing liquid via the spray holes.

In one implementation of the present disclosure, the fixing member may have a sensor for measuring an impact force from the outside and transmitting the measured result to a controller, and the controller may control to spray the sterilizing liquid using the sterilizing liquid supplier when the measured impact force reaches a reference impact force.

In one implementation of the present disclosure, a wrinkle layer may be further formed between the fixing member and the sealing member.

In one implementation of the present disclosure, a bottom surface of the sealing member may be formed as a upwardly convex curved surface. A lower space may be defined below the sealing member as the curved surface is formed.

In one implementation of the present disclosure, a discharge module may be installed on the fixing member. The discharge module may be connected to the lower space of the sealing member via a discharge tube. The discharge tube may be disposed inside the fixing member and the sealing member, and a distal end of the discharge tube may be exposed to the internal space. The discharge module may be driven under control of the controller. The discharge tube may be connected to a filter.

In one implementation of the present disclosure, when the measured impact force reaches a reference impact force, the controller may use the discharge module to forcibly suck in air containing foreign substances existing in the lower space via the discharge tube, filter the foreign substances via the filter, and discharge the filtered air to the outside.

In one implementation of the present disclosure, a photocatalyst containing titanium oxide for sterilization may be further contained in the fixing member, the sealing member, and the discharge tube.

In one implementation of the present disclosure, a colored layer may be formed on outer surfaces of the fixing member and the sealing member, a line-shaped sterilizing light module may be embedded in the fixing member and the sealing member, and the sterilizing light module may emit UV light within a predetermined power range under control of the controller.

In one implementation of the present disclosure, a vibration module may be connected to the sealing member, and the vibration module may vibrate the sealing member to achieve a set frequency under control of the controller.

In one implementation of the present disclosure, the controller may drive the vibration module a predetermined time before the discharge module is operated.

Another aspect of the present disclosure provides a hinged door structure including the door sealing unit for preventing spread of the harmful gases and the viruses.

According to the embodiment of the present disclosure, as the door sealing unit is easily installed on the lower end frame of the hinged door in the sliding manner and the sealing members of the soft material are used for the multiple contact with the floor to improve the contact properties, the spread of the infectious disease viruses may be prevented.

In addition, according to the embodiment of the present disclosure, the lower end frame of the door and the floor are uniformly in close contact with each other regardless of the evenness of the floor surface of the room.

In addition, according to the embodiment of the present disclosure, as the foreign substances present on the floor to which the sealing members are contacted are removed, the contact properties between sealing members and the floor may be improved and the space between the sealing members may be ventilated, so that, even when the infectious bacteria infiltrate into the space between the sealing members from inside the room, the bacteria may be removed by being discharged to the outside space without spreading to the living room.

In addition to the above-described effects, specific effects of the present disclosure will be described together while describing specific details for implementing the invention below.

Effects of the present disclosure are not limited to the effects mentioned above, and other effects not mentioned will be clearly understood by those skilled in the art from the descriptions below.

DETAILED DESCRIPTIONS

Figure 1:
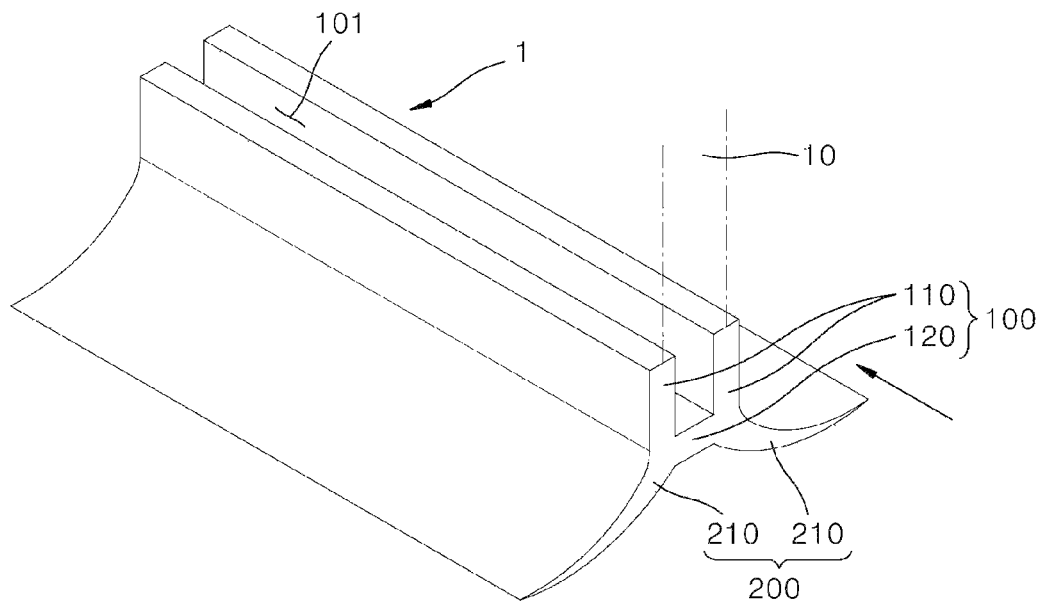
FIG. 1 is a perspective view showing a door sealing unit for preventing spread of harmful gases and viruses according to the present disclosure.

Advantages and features of the present disclosure, and a method of achieving the advantages and features will become apparent with reference to embodiments described later in detail together with the accompanying drawings. However, the present disclosure is not limited to the embodiments as disclosed under, but may be implemented in various different forms. Thus, these embodiments are set forth only to make the present disclosure complete, and to completely inform the scope of the present disclosure to those of ordinary skill in the technical field to which the present disclosure belongs, and the present disclosure is only defined by the scope of the claims.

For simplicity and clarity of illustration, elements in the drawings are not necessarily drawn to scale. The same reference numbers in different drawings represent the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure. Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

A shape, a size, a ratio, an angle, a number, etc. disclosed in the drawings for describing embodiments of the present disclosure are illustrative, and the present disclosure is not limited thereto. The same reference numerals refer to the same elements herein. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

The terminology used herein is directed to the purpose of describing particular embodiments only and is not intended to be limiting of the present disclosure. As used herein, the singular constitutes "a" and "an" are intended to include the plural constitutes as well, unless the context clearly indicates otherwise. It will be further understood that the terms "comprise", "including", "include", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of associated listed items. Expression such as "at least one of" when preceding a list of elements may modify the entire list of elements and may not modify the individual elements of the list. In interpretation of numerical values, an error or tolerance therein may occur even when there is no explicit description thereof.

In addition, it will also be understood that when a first element or layer is referred to as being present "on" a second element or layer, the first element may be disposed directly on the second element or may be disposed indirectly on the second element with a third element or layer being disposed between the first and second elements or layers. It will be understood that when an element or layer is referred to as being "connected to", or "connected to" another element or layer, it may be directly on, connected to, or connected to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Further, as used herein, when a layer, film, region, plate, or the like is disposed "on" or "on a top" of another layer, film, region, plate, or the like, the former may directly contact the latter or still another layer, film, region, plate, or the like may be disposed between the former and the latter. As used herein, when a layer, film, region, plate, or the like is directly disposed "on" or "on a top" of another layer, film, region, plate, or the like, the former directly contacts the latter and still another layer, film, region, plate, or the like is not disposed between the former and the latter. Further, as used herein, when a layer, film, region, plate, or the like is disposed "below" or "under" another layer, film, region, plate, or the like, the former may directly contact the latter or still another layer, film, region, plate, or the like may be disposed between the former and the latter. As used herein, when a layer, film, region, plate, or the like is directly disposed "below" or "under" another layer, film, region, plate, or the like, the former directly contacts the latter and still another layer, film, region, plate, or the like is not disposed between the former and the latter.

In descriptions of temporal relationships, for example, temporal precedent relationships between two events such as "after", "subsequent to", "before", etc., another event may occur therebetween unless "directly after", "directly subsequent" or "directly before" is not indicated.

When a certain embodiment may be implemented differently, a function or an operation specified in a specific block may occur in a different order from an order specified in a flowchart. For example, two blocks in succession may be actually performed substantially concurrently, or the two blocks may be performed in a reverse order depending on a function or operation involved.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described under could be termed a second element, component, region, layer or section, without departing from the spirit and scope of the present disclosure.

The features of the various embodiments of the present disclosure may be partially or entirely combined with each other, and may be technically associated with each other or operate with each other. The embodiments may be implemented independently of each other and may be implemented together in an association relationship.

In interpreting a numerical value, the value is interpreted as including an error range unless there is no separate explicit description thereof.

It will be understood that when an element or layer is referred to as being "connected to", or "connected to" another element or layer, it may be directly on, connected to, or connected to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

The features of the various embodiments of the present disclosure may be partially or entirely combined with each other, and may be technically associated with each other or operate with each other. The embodiments may be implemented independently of each other and may be implemented together in an association relationship.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, "embodiments," "examples," "aspects," and the like should not be construed such that any aspect or design as described is superior to or advantageous over other aspects or designs.

Further, the term 'or' means 'inclusive or' rather than 'exclusive or'. That is, unless otherwise stated or clear from the context, the expression that 'x uses a or b' means any one of natural inclusive permutations.

The terms used in the description below have been selected as being general and universal in the related technical field. However, there may be other terms than the terms depending on the development and/or change of technology, convention, preference of technicians, etc. Therefore, the terms used in the description below should not be understood as limiting technical ideas, but should be understood as examples of the terms for describing embodiments.

Further, in a specific case, a term may be arbitrarily selected by the applicant, and in this case, the detailed meaning thereof will be described in a corresponding description section. Therefore, the terms used in the description tion below should be understood based on not simply the name of the terms, but the meaning of the terms and the contents throughout the Detailed Descriptions.

The following describes a door sealing unit for preventing spread of harmful gases and viruses according to the present disclosure with reference to the accompanying drawings.

The door sealing unit according to the present disclosure is used by being installed on a lower end frame of a hinged door. In addition, the present disclosure provides a hinged door structure equipped with the above-described door sealing unit. The hinged door structure has the door sealing unit according to the present disclosure installed on the lower end frame of the door and the door. The door sealing unit may be formed integrally with the door, or may be detachably installed on the lower end frame of the door in a sliding manner. In the following description, the door sealing unit according to the present disclosure will be described, but an example in which the door sealing unit is fitted onto the lower end frame of the door will be described as a representative example.

Figure 2:
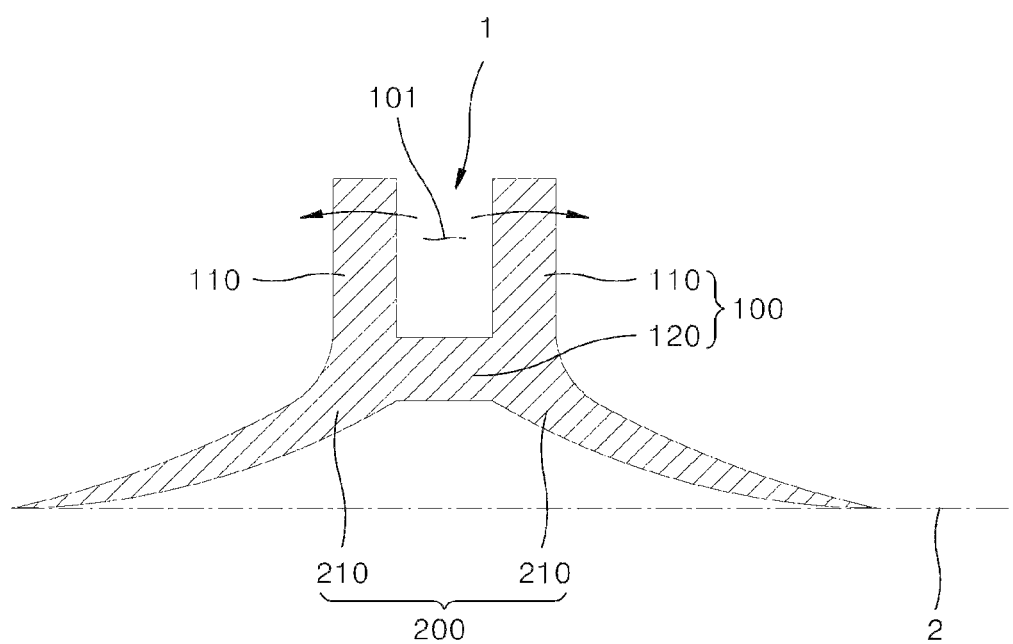
FIG. 2 is a cross-sectional view showing a door sealing unit in FIG. 1.

FIG. 1 is a perspective view showing a door sealing unit for preventing spread of harmful gases and viruses according to the present disclosure. FIG. 2 is a cross-sectional view showing a door sealing unit in FIG. 1.

With reference to FIGS. 1 and 2, a configuration of the door sealing unit 1 according to the present disclosure will be described.

The door sealing unit 1 according to the present disclosure has a fixing member 100 and a sealing member 200. The fixing member 100 and the sealing member 200 are formed as one body. The door sealing unit 1 may be made of a soft material, and may be made of silicone rubber. Accordingly, the door sealing unit 1 may have a predetermined amount of elasticity and may be flexibly deformed in shape.

The fixing member 100 has a predetermined length. A groove 101 is defined in the fixing member 100. The groove 101 is defined as a U-shaped groove such that an upper side and both sides of the fixing member 100 are opened.

Accordingly, the fixing member 100 has a pair of wall members 110 to define the groove 101 therebetween and a base member 120 to form a bottom of the pair of wall members 110. Accordingly, the groove 101 is defined between the pair of wall members 110 and the base member 120.

Further, a distance between the pair of wall members 110 is gradually reduced in an upward direction. That is, a width of the groove 101 is reduced in the upward direction. Accordingly, the pair of wall members 110 are formed to be inclined at a predetermined angle along a direction facing each other.

In one example, as the fixing member 100 is made of the soft material, the fixing member 100 may spread, and may return to an original state thereof with an elastic restoring force thereof from the spread state.

In this regard, the groove 101 defined in the fixing member 100 is used for fitting the lower end frame of the door therein. in addition, the fixing member 100 may be slidingly fitted onto the lower end frame of the door via a side portion of the lower end frame of the door.

On the other hand, the sealing member 200 is formed integrally with a lower end of the fixing member 100.

The sealing member 200 is formed to spread to both sides with the fixing member 100 as a boundary. Accordingly, the sealing member 200 is composed of a pair of unit seal members 210 formed to form symmetry with the fixing member 100 as the boundary.

A thickness of the unit seal member 210 gradually becomes thinner toward a distal end thereof. The sealing member 200 may have a length equal to that of the fixing member 100.

The unit seal members 210 may spread to both sides and come into contact with a floor 2 in the spread state.

Figure 3:
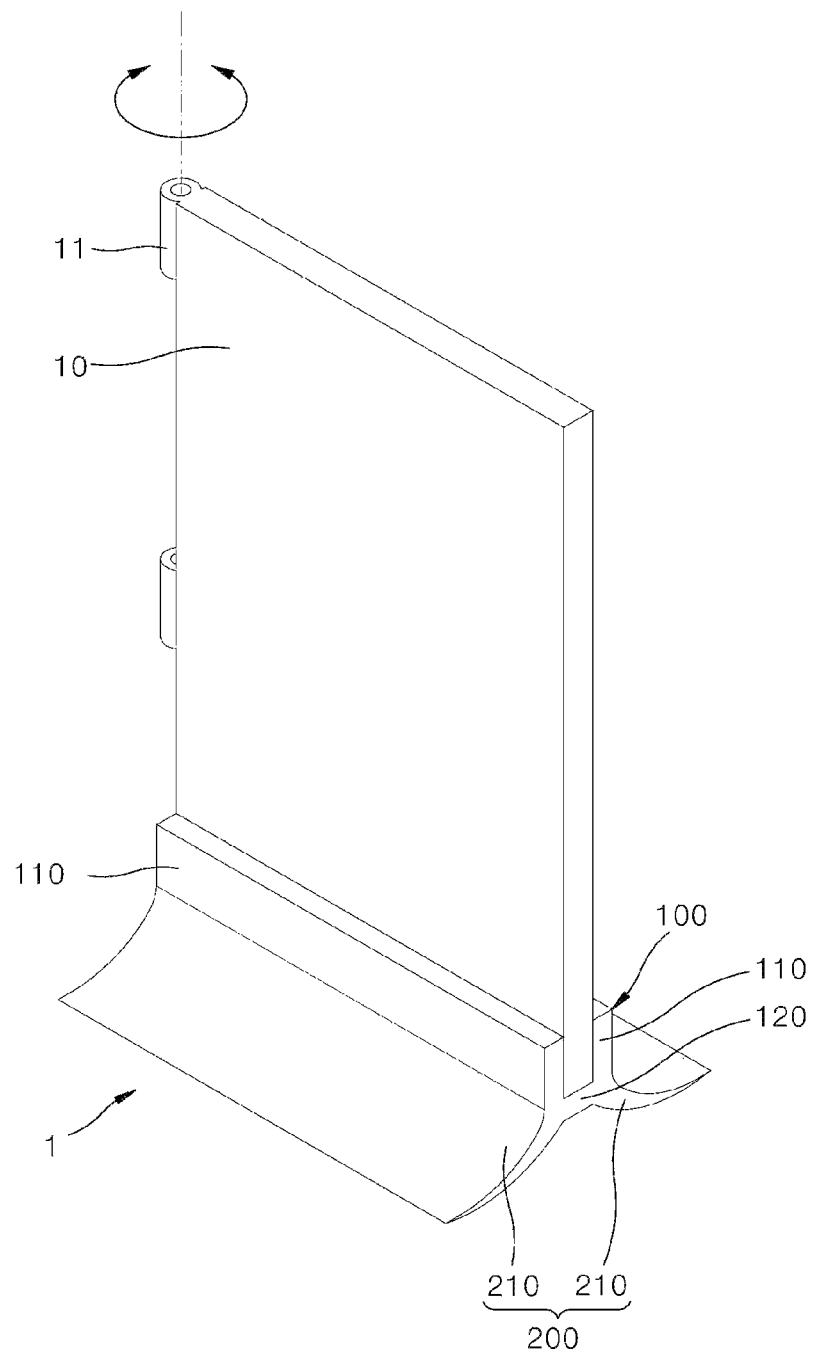
FIG. 3 is a perspective view showing a state in which a door sealing unit is installed on a lower end frame of a door, according to the present disclosure.

FIG. 3 is a perspective view showing a state in which a door sealing unit is installed on a lower end frame of a door, according to the present disclosure.

Referring to FIG. 3, a door 10 may be a door for the rom of each household. A door frame (not shown) is installed on a wall surface of the room. The door 10 is installed to be pivotably opened and closed in a hinged manner on the door frame via a hinge 11. In this regard, a predetermined gap is defined between a lower end frame of the door 10 and the floor 2.

The fixing member 100 of the door sealing unit 1 may be installed on the lower end frame of the door 10 in the sliding manner. The pair of wall members 110 may achieve a retracted state. The pair of wall members 110 may spread to have a width equal to or greater than a predetermined width to insert the lower end frame of the door 10 into the groove 101 in the sliding manner.

Then, the pair of wall members 110 are returned to the original state thereof by the elastic restoring force. As a result, inner peripheral surfaces of the pair of wall members 110 achieve a predetermined elastic force and are fixed in close contact with both side surfaces of the lower end frame of the door 10, and a lower end of the lower end frame of the door 10 is in close contact with a bottom surface of the groove 101.

Therefore, as the groove 101 of the fixing member 100 is fitted onto the lower end frame of the door 10 in the sliding manner, the door sealing unit 1 according to the present disclosure may be installed in close contact with the lower end frame of the door 10.

In this regard, the pair of unit seal members 210 spread to both sides of the sealing member 200 may achieve a state in contact with the floor in the spread state. In this regard, a predetermined gap may be maintained between a lower end of the base member 120 and the floor.

An operation of the door sealing unit according to the present disclosure installed in this manner will be described.

Figure 4A:
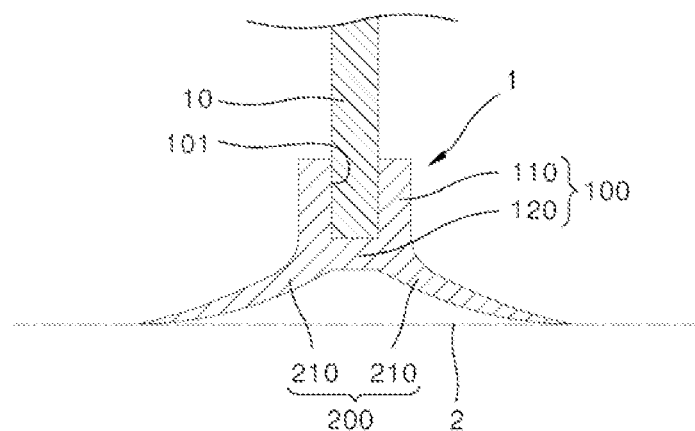
FIGS. 4A to 4C are cross-sectional views showing behavior states of a door sealing unit based on opening and closing of a door.
Figure 4B:
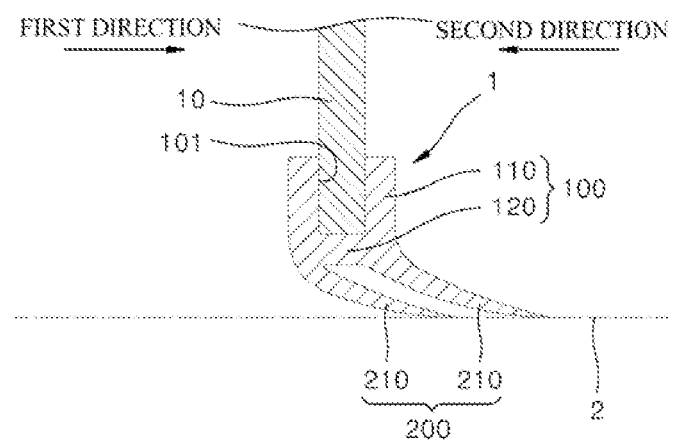
Figure 4C:
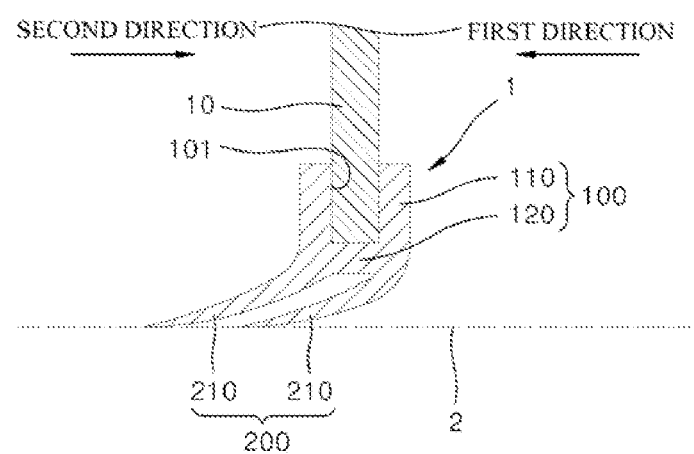

FIGS. 4A to 4C are cross-sectional views showing behavior states of a door sealing unit based on opening and closing of a door.

(a) in FIG. 4A shows an initial state before the opening and closing operation of the door 10 is performed after the door sealing unit 1 is installed on the lower end frame of the door 10.

(b) in FIG. 4B shows a behavior of the door sealing unit 1 when the door 10 is open.

The door 10 may be pivoted along a first direction to open as shown in (b) in FIG. 4B from the state of (a).

In this regard, the unit seal member 210 on one side among the pair of unit seal members 210 of the sealing member 200 is bent while being swept to the floor along a second direction, which is a reverse direction of the direction in which the door 10 is pivoted.

Further, a distal end of the bent unit seal member 210 on one side is bent toward the unit seal member 210 on the other side while being curled along the second direction to achieve a state in which an outer peripheral surface of the unit seal member is in close contact with the floor 2.

(c) in FIG. 4C shows a behavior of the sealing unit when the door 10 is closed.

On the other hand, when the door 10 is closed from the state of (b) in FIG. 4B to a state of (c) in FIG. 4C, the unit seal member 210 on the other side among the pair of unit seal members 210 of the sealing member 200 is pivoted while being swept to the floor 2 along a first direction, which is the reverse direction of the second direction in which the door 10 is pivoted to be closed. Further, an outer peripheral surface of the unit seal member 210 on the other side achieves a state of being in close contact with the floor 2.

Further, a distal end of the bent unit seal member 210 on one side is curled in reverse along the first direction and spreads toward the first direction to return to the original shape thereof, and a bottom surface of the bent unit seal member 210 on one side achieves the state of being in close contact with the floor 2.

Accordingly, the door sealing unit 1 according to the present disclosure may be deformed in shape to be in close contact with the floor as the door 10 is opened and closed.

At the same time, the pair of unit seal members 210 extending from the fixing member 100 are in close contact with the floor while having the predetermined width, so that the gap between the lower end frame of the door 10 and the floor 2 may be easily sealed.

Therefore, when an infected person self-isolates in the room, viruses that cause infection may be effectively prevented from spreading to areas such as the living room, which is a space outside the door, via the gap between the door lower end frame and the floor.

Figure 5:
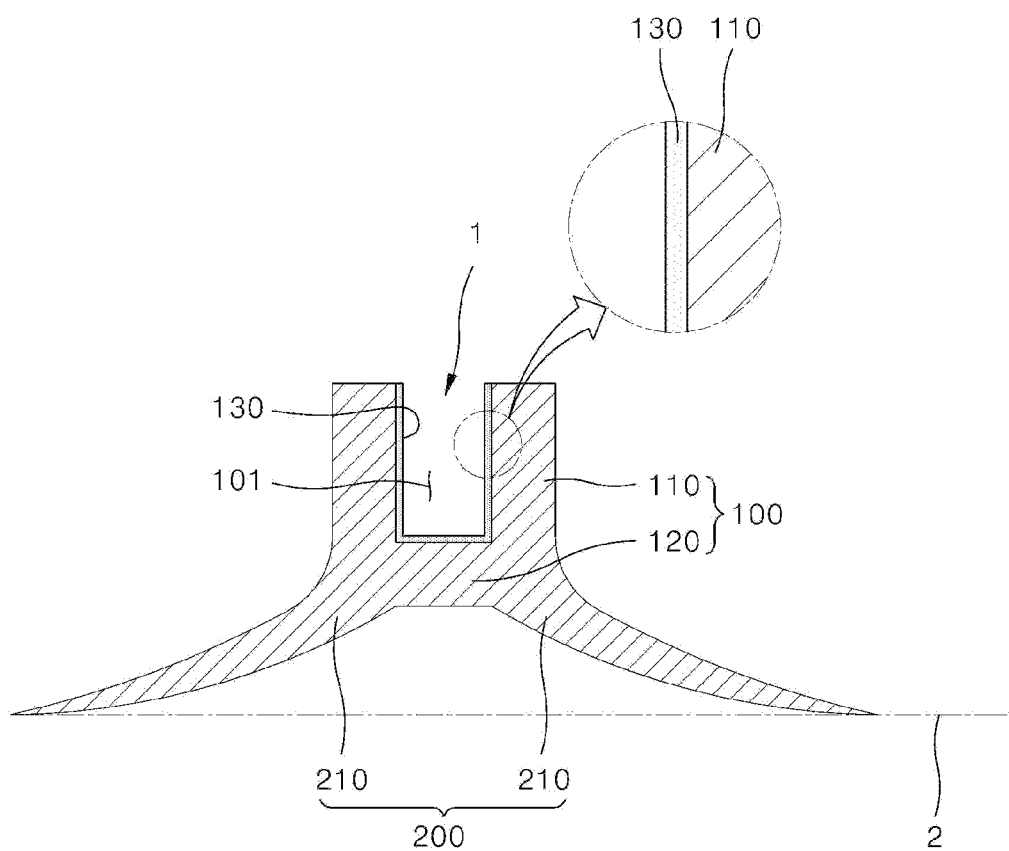
FIG. 5 is a cross-sectional view showing an example in which a lubricating oil coating layer is further formed in a groove defined in a fixing member of a sealing unit according to the present disclosure.

FIG. 5 is a cross-sectional view showing an example in which a lubricating oil coating layer is further formed in a groove defined in a fixing member of a sealing unit according to the present disclosure.

Referring to FIG. 5, a lubricating oil coating layer 130 is formed on an inner wall of the groove 101 defined in the fixing member 100 of the door sealing unit 1.

The lubricating oil coating layer 130 may be formed as a layer having a predetermined thickness on an inner peripheral surface of the groove 101 at a time of preparation.

The lubricating oil coating layer 130 may induce slip. The groove 101 is the portion into which the lower end frame of the door 10 is inserted in the sliding manner via the side portion thereof.

In this regard, the slip may occur as both side surfaces and a lower end surface of the lower end frame of door 10 come into contact with the lubricating oil coating layer 130 formed on the inner peripheral surface of the groove 101.

Accordingly, the lower end frame of the door 10 may be easily inserted into the groove 101 of the fixing member 100.

In one example, as the pair of wall members 110 are retracted, an elastic compression force may be applied to both side surfaces of the lower end frame of the door 10, and the fixing member 100 may be easily fixed to the lower end frame of the door 10.

In the above example, the formation of the lubricating oil coating layer 130 on the inner peripheral surface of the groove 101 has been described as the representative example. Although not shown in the drawings, multiple rib-shaped protrusion lines along a longitudinal direction of the fixing member 100 may be formed on the inner peripheral surface of the groove 101 to induce the sliding insertion. That is, only the protrusion lines are made to be in contact with the outer peripheral surface of the lower end frame of the door 10 to minimize a frictional force during the sliding insertion, thereby inducing the slip.

Further, when the pair of wall members 110 are retracted and the inner peripheral surface of the groove 101 is in close contact with the outer peripheral surface of the lower end frame of the door 10, because the protrusion lines are also made of a soft material, the protrusion lines spread and easily come into close contact with the outer peripheral surface of the lower end frame of the door 10 to form a fixing force of a level equal to or higher than a predetermined level.

Figure 6:
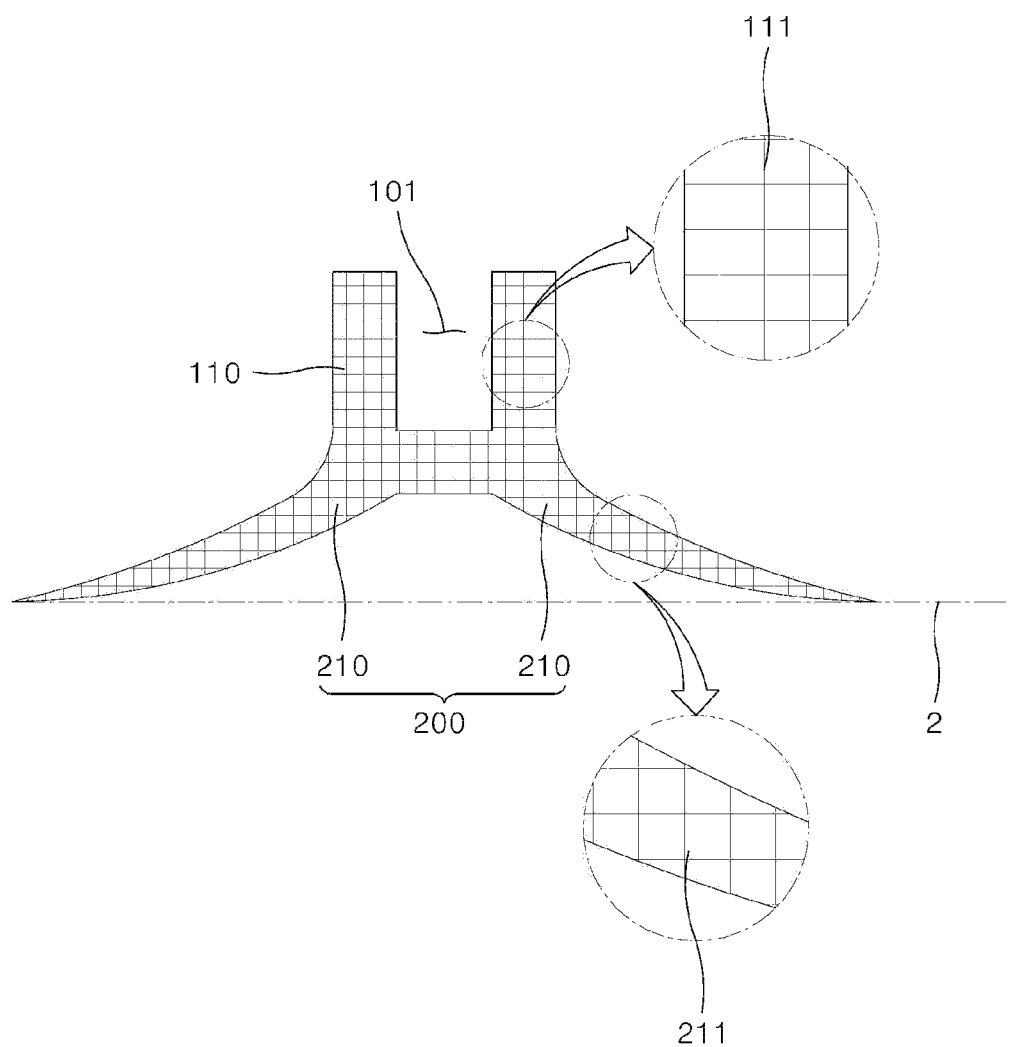
FIG. 6 is a view showing an example in which a grid-shaped inner structure is formed inside a fixing member and a sealing member according to the present disclosure.

FIG. 6 is a view showing an example in which a grid-shaped inner structure is formed inside a fixing member and a sealing member according to the present disclosure.

Referring to FIG. 6, the fixing member 100 and the sealing member 200 according to the present disclosure are formed integrally with each other.

A first inner structure 111 is formed inside the fixing member 100, and a second inner structure 211 is formed inside the sealing member 200. The first and second inner structures 111 and 211 may be formed in a grid shape. In one example, the first and second inner structures 111 and 211 may be formed in a hexagonal honeycomb shape or a polygonal shape in addition to the grid shape as described above.

In this regard, a density of the first inner structure 111 of the fixing member 100 may be greater than that of the second inner structure 211 of the sealing member 200.

Accordingly, a strength of the fixing member 100 may be greater than that of the sealing member 200 by a predetermined amount or more. That is, the lower end frame of the door 10 is inserted into the groove 101 of the fixing member 100 in the sliding manner.

In this regard, the pair of wall members 110 of the fixing member 100 may be elastically in contact with both side surfaces of the lower end frame of the door 10 and fixed to the lower end frame of the door 10, and may have a strength equal to or greater than a predetermined level, so that the fixing force described above may be improved to a level equal to or higher than a predetermined level.

Therefore, even when the sealing member 200 is swept to and come into contact with the floor while repeatedly changing a direction during the repeated opening and closing of the door 10, a position thereof fixed to the lower end frame of the door 10 may not be changed.

On the other hand, the sealing member 200 is the member whose shape is repeatedly deformed in contact with the floor. The sealing member 200 may be easily deformed by the second inner structure 211 formed therein, and may solve a problem that a local area thereof is damaged by the repeated deformation.

Figure 7:
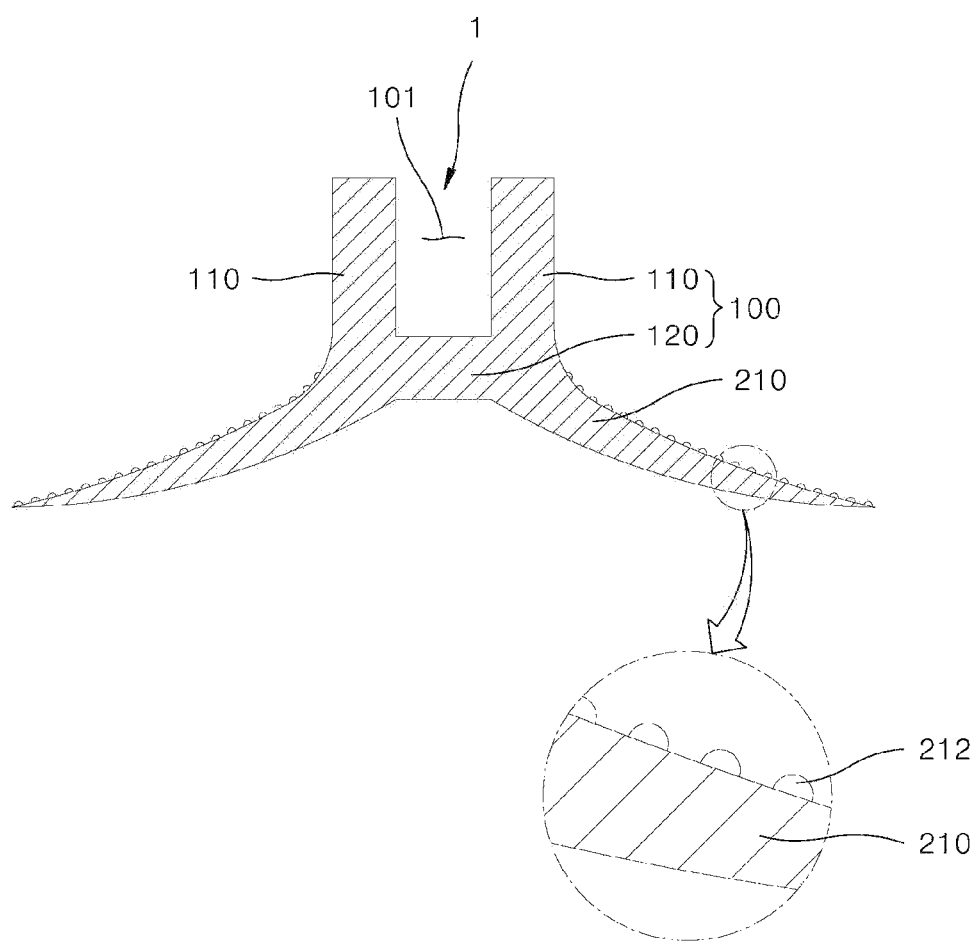
FIG. 7 is a view showing an example in which embossed protrusions are formed on a top outer surface of a sealing member according to the present disclosure.

FIG. 7 is a view showing an example in which embossed protrusions are formed on a top outer surface of a sealing member according to the present disclosure.

Referring to FIG. 7, embossed protrusions 212 are formed to protrude from top outer surfaces of the pair of unit seal members 210 in the sealing member 200 according to the present disclosure.

In this regard, when the door 10 is opened or closed, substantially the top outer surfaces of the pair of unit seal members 210 may be an area in contact with the floor.

Therefore, when the shape of each unit seal member 210 is deformed such that the top outer surface of each unit seal member 210 is in contact with the floor, the embossed protrusions 212 may be in elastic contact with the floor and may be moved while sweeping the floor.

Accordingly, the embossed protrusions 212 may serve to improve a force of contact with the floor and to easily guide the shape deformation while the shape of each unit seal member 210 is deformed based on the pivoting of the door.

Figure 8:
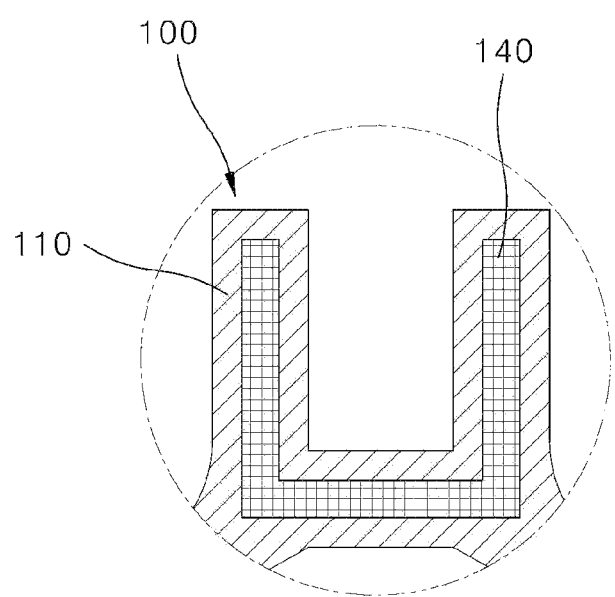
FIG. 8 is a diagram showing an example in which an elastic wire mesh is embedded inside a fixing member according to the present disclosure.

FIG. 8 is a diagram showing an example in which an elastic wire mesh is embedded inside a fixing member according to the present disclosure.

Referring to FIG. 8, the fixing member 100 according to the present disclosure may be made of the soft material, and may spread the pair of wall members 110 when being fitted onto the lower end frame of the door.

In this regard, a wire mesh 140 made of an elastic material may be embedded inside the fixing member 100. Because the wire mesh 140 has an elasticity of a predetermined level, the wire mesh 140 may maintain or restore the original shape of the fixing member.

Further, it is preferable that the elastic force of the wire mesh 140 has a level higher than that of the fixing member 100 itself by a predetermined amount or more.

Accordingly, even when the fixing member 100 is repeatedly deformed, the fixing member 100 may be easily returned to the original shape thereof by the elastic force of the wire mesh 140 itself, and may be easily fixed to the lower end frame of the door.

Figure 9:
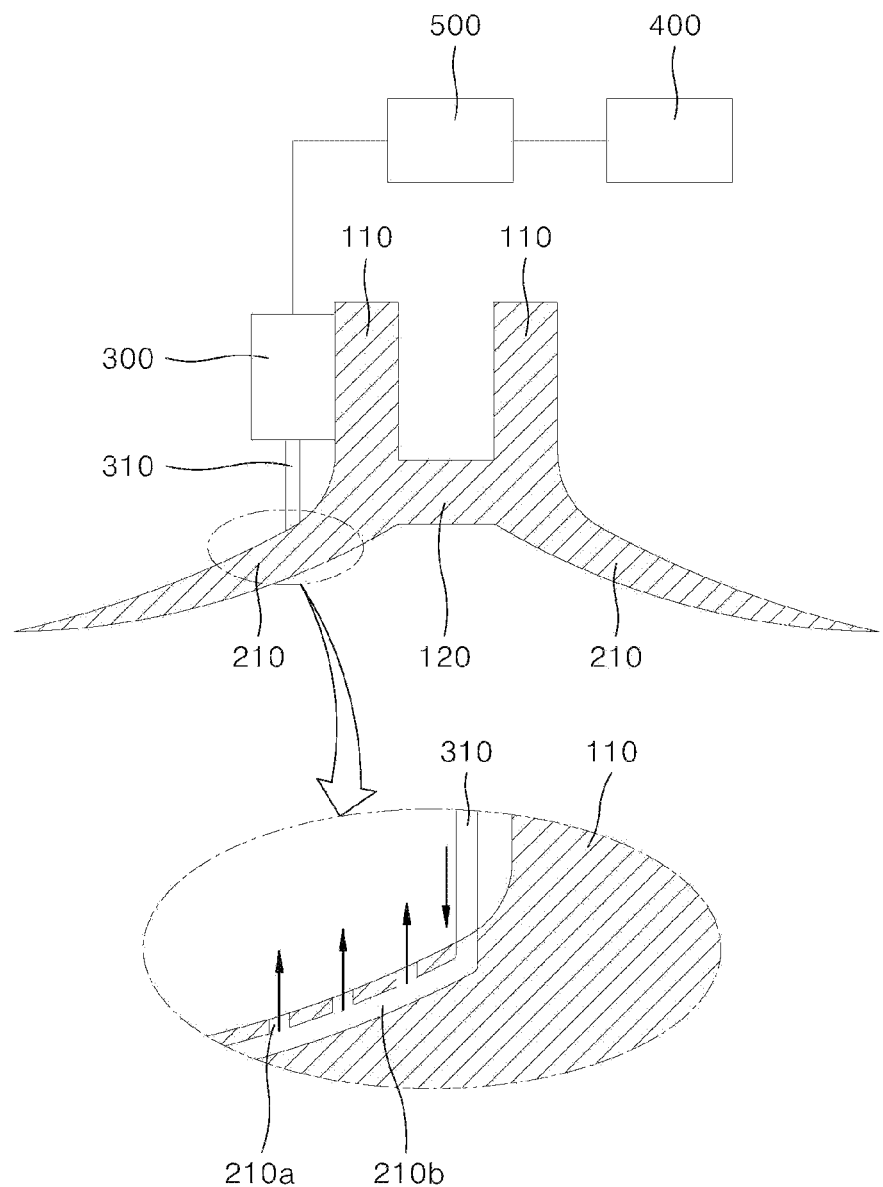
FIG. 9 is a view showing an example of a configuration in which a door sealing unit can spray sterilizing liquid, according to the present disclosure.
Figure 10:
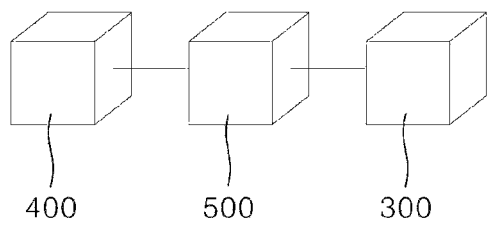
FIG. 10 is a block diagram showing a control flow for sterilizing liquid spray.

FIG. 9 is a view showing an example of a configuration in which a door sealing unit can spray sterilizing liquid, according to the present disclosure. FIG. 10 is a block diagram showing a control flow for sterilizing liquid spray.

Referring to FIG. 9, a sterilizing liquid supplier 300 that supplies sterilizing liquid is detachably installed on the fixing member 100 according to the present disclosure. The detachment may be performed using a hook or an adhesive tape.

Spray holes 210a are defined in an outer peripheral surface of the sealing member 200.

Supply holes 210b connected to the spray holes 210a are defined in the fixing member 100 and the sealing member 200.

The sterilizing liquid supplier 300 may be connected to one end of the supply holes 210b via a tube 310, and when a set period is reached, supply the sterilizing liquid via the tube 310 and the supply hole 210b and spray the sterilizing liquid via the spray holes 210a.

Referring to FIG. 10, the fixing member 100 has a sensor 400 that measures an impact force from the outside and transmits the measurement result to a controller 500.

The controller 500 may control to spray the sterilizing liquid using the sterilizing liquid supplier 300 when the measured impact force reaches a reference impact force.

Figure 11:
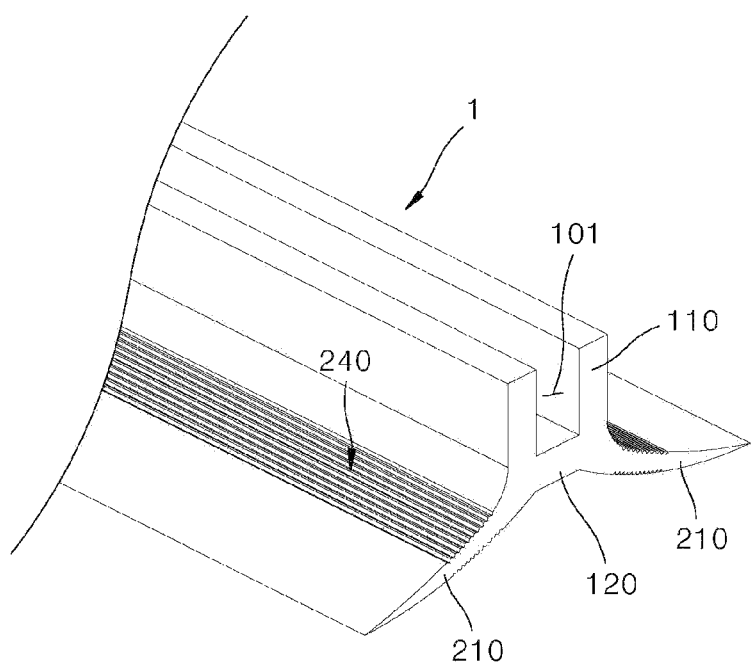
FIG. 11 is a diagram showing an example in which a wrinkle layer is further formed on a boundary between a fixing member and a sealing member according to the present disclosure.

FIG. 11 is a diagram showing an example in which a wrinkle layer is further formed on a boundary between a fixing member and a sealing member according to the present disclosure.

Referring to FIG. 11, a wrinkle layer 240 may be further formed at a boundary between the fixing member 100 and the sealing member 200.

Accordingly, when each unit seal member 210 repeatedly changes the direction thereof while being in contact with the floor, because such wrinkle layer 240 follows a longitudinal direction of the sealing member 200 and is formed on top and bottom surfaces of the sealing member 200, the bending may be easily guided.

Figure 12:
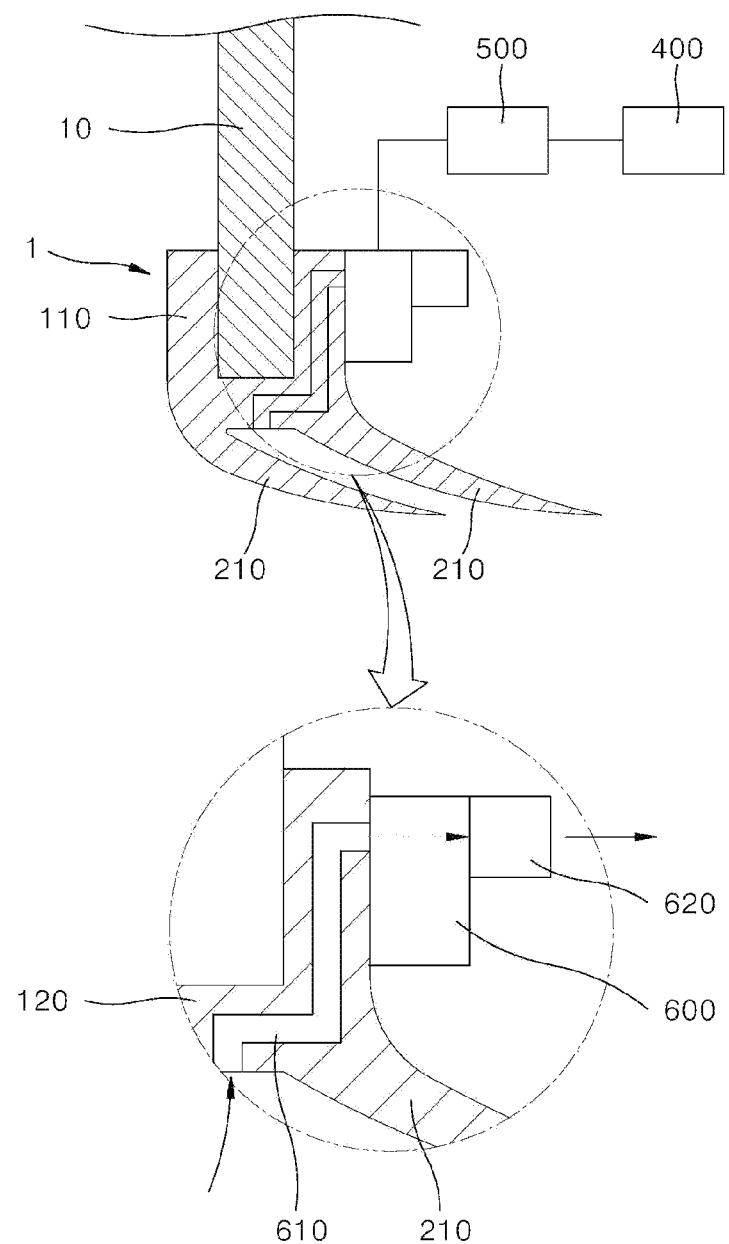
FIG. 12 is a view showing an example having a discharge module capable of removing foreign substances existing in a lower space of a sealing member according to the present disclosure.

FIG. 12 is a view showing an example having a discharge module capable of removing foreign substances existing in a lower space of a sealing member according to the present disclosure.

Referring to FIG. 12, the lower end surface of the sealing member 200 is formed as an upwardly convex curved surface. As the curved surface is formed, a lower space is defined below the sealing member 200.

A discharge module 600 is installed on the fixing member 100. The discharge module 600 is connected to the lower space of the sealing member 200 via a discharge tube 610. The discharge tube 610 is disposed inside the fixing member 100 and the sealing member 200, and a distal end of the discharge tube 610 is exposed to the inner space. The discharge module 600 is driven under control of the controller 500. The discharge tube 610 is connected to a filter 620.

Accordingly, when the measured impact force reaches a reference impact force, the controller 500 may use the discharge module 600 to forcibly suck in air containing foreign substances existing in the lower space via the discharge tube 610, filter the foreign substances via the filter 620, and discharge the filtered air to the outside.

Figure 13:
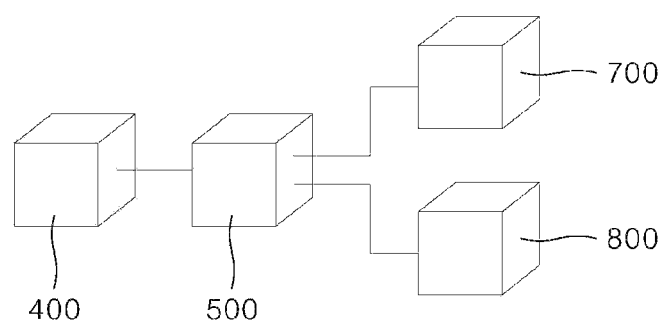
FIG. 13 is a block diagram showing a control flow to forcibly remove foreign substances present in a sealing member according to the present disclosure.

FIG. 13 is a block diagram showing a control flow to forcibly remove foreign substances present in a sealing member according to the present disclosure.

Referring to FIG. 13, the fixing member 100, the sealing member 200, and the discharge tube 610 according to the present disclosure further include a photocatalyst (not shown) containing titanium dioxide for sterilization.

The photocatalyst is a compound that absorbs light energy to initiate a photochemical reaction and promotes the photochemical reaction as a catalyst. A typical photocatalyst is titanium dioxide $TiO_2$, which is used for photolysis of water to obtain hydrogen and oxygen gases.

Accordingly, when there is light of an amount equal to or greater than a predetermined amount in the room with the door closed for the self-isolation indoors, the photocatalyst coated on or contained in the sealing member 200 performs air purification and sterilization in the space between the lower end frame of the door and the floor to keep safety when infectious bacteria spread to the outside of the door.

Further, a colored layer (not shown) may be formed on outer surfaces of the fixing member 100 and the sealing member 200. This makes it possible to block direct exposure of UV light emitted from a sterilizing light module 700, which will be described later, into the room.

The line-shaped sterilizing light module 700 may be installed inside the fixing member 100 and the sealing member 200.

The sterilizing light module 700 emits the UV light within a predetermined power range under control of the controller 500.

In addition, a vibration module 800 may be connected to the sealing member 200, and the vibration module 800 may vibrate the sealing member 200 to achieve a set frequency under control of the controller 500.

Accordingly, the controller 500 drives the vibration module 800 before a predetermined time before the discharge module 600 is operated.

Accordingly, the foreign substances present in the sealing member may be shaken off via vibration by driving the vibration module before the predetermined time before the foreign substances are discharged via the discharge module.

Then, the controller may use the discharge module to forcibly discharge the foreign substances including the foreign substances that have been shaken off to the outside.

Therefore, the present disclosure improves the contact properties between the sealing members and the floor by removing the foreign substances present on the floor to which the sealing members are contacted, and allows the space between the sealing members to be ventilated, so that, even when the infectious bacteria infiltrate into the space between the sealing members from inside the room, the bacteria may be removed by being discharged to the outside space without spreading to the living room.

Although the embodiments of the present disclosure have been described in more detail with reference to the accompanying drawings, the present disclosure is not necessarily limited to these embodiments, and may be modified in a various manner within the scope of the technical spirit of the present disclosure. Accordingly, the embodiments as disclosed in the present disclosure are intended to describe rather than limit the technical idea of the present disclosure, and the scope of the technical idea of the present disclosure is not limited by these embodiments. Therefore, it should be understood that the embodiments described above are not restrictive but illustrative in all respects.

What is claimed is:

1. A door sealing unit for preventing spread of harmful gases and viruses installed on a lower end frame of a door installed in a hinged manner at a boundary between a living room and a room, the door sealing unit for preventing spread of harmful gases and viruses comprising:
    a fixing member having a predetermined amount of elasticity and fixed onto the lower end frame of the door; and
    a sealing member formed on a lower end of the fixing member and made of a silicone rubber, wherein the sealing member is composed of a pair of unit seal members formed symmetrically with the fixing member and come into contact with a floor in a spread state,
    wherein a groove for receiving the lower end frame of the door fitted thereinto in a sliding manner is defined in the fixing member,
    wherein a lubricating oil coating layer is further formed on an inner peripheral surface of the groove,
    wherein a sterilizing liquid supplier for supplying sterilizing liquid is detachably installed on the fixing member,
    wherein spray holes are defined in an outer peripheral surface of the sealing member,
    wherein supply holes connected to the spray holes are defined in the fixing member and the sealing member, and
    wherein the sterilizing liquid supplier is connected to one end of each of the supply holes via a tube, and, when a set period is reached, supplies the sterilizing liquid via the tube and the supply hole and sprays the sterilizing liquid via the spray holes.

2. The door sealing unit for preventing spread of harmful gases and viruses of claim 1, wherein a grid-shaped inner structure is formed inside the fixing member and the sealing member,
    wherein a density of the inner structure is greater in the fixing member than in the sealing member.

3. The door sealing unit for preventing spread of harmful gases and viruses of claim 1, wherein a bottom surface of the sealing member forms a flat surface.

4. The door sealing unit for preventing spread of harmful gases and viruses of claim 1, wherein embossed protrusions are formed on a top outer surface of the sealing member.

5. The door sealing unit for preventing spread of harmful gases and viruses of claim 1, wherein an elastic wire mesh is embedded in the fixing member.

6. The door sealing unit for preventing spread of harmful gases and viruses of claim 1, wherein the fixing member is provided with a sensor for measuring an impact force from the outside and transmitting the measured result to a controller,
    wherein the controller is configured to control the spraying of the sterilizing liquid using the sterilizing liquid supplier when the measured impact force reaches a reference impact force.

* * * * *